United States Patent
Wu et al.

(10) Patent No.: US 11,116,803 B2
(45) Date of Patent: Sep. 14, 2021

(54) **METHOD OF TREATING LUNG CANCER USING *PARABACTEROIDES GOLDSTEINII***

(71) Applicant: Multistars Biotechnology Company Limited, Taoyuan (TW)

(72) Inventors: Po-I Wu, Taoyuan (TW); Chih-Jung Chang, Taoyuan (TW); Yu-Ling Tsai, Taoyuan (TW)

(73) Assignee: MULTISTARS BIOTECHNOLOGY COMPANY LIMITED, Taoyuan (TW)

( * ) Notice: Subject to any disclaimer, the term of this patent is extended or adjusted under 35 U.S.C. 154(b) by 90 days.

(21) Appl. No.: 16/667,950

(22) Filed: Oct. 30, 2019

(65) Prior Publication Data

US 2020/0129568 A1    Apr. 30, 2020

Related U.S. Application Data

(60) Provisional application No. 62/753,112, filed on Oct. 31, 2018.

(30) Foreign Application Priority Data

Oct. 23, 2019 (TW) .................................. 108138285

(51) Int. Cl.
| | | |
|---|---|---|
| A61K 35/74 | (2015.01) | |
| A23L 29/00 | (2016.01) | |
| A61K 9/00 | (2006.01) | |
| A61P 35/00 | (2006.01) | |

(52) U.S. Cl.
CPC ............ *A61K 35/74* (2013.01); *A23L 29/065* (2016.08); *A61K 9/0053* (2013.01); *A61P 35/00* (2018.01)

(58) Field of Classification Search
None
See application file for complete search history.

(56) References Cited

FOREIGN PATENT DOCUMENTS

WO    WO-2018112363 A1 *   6/2018   ............. A61K 35/17

* cited by examiner

*Primary Examiner* — Brian Gangle
(74) *Attorney, Agent, or Firm* — WPAT, PC (57) ABSTRACT

The present disclosure provides a use of *Parabacteroides goldsteinii* for treating lung cancer.

12 Claims, 5 Drawing Sheets

METHOD OF TREATING LUNG CANCER USING *PARABACTEROIDES GOLDSTEINII*

CROSS-REFERENCE TO RELATED APPLICATION

This application claims priority of U.S. provisional application No. 62/753,112, filed on Oct. 31, 2018, and priority of Taiwan patent application No. 108138285, filed on Oct. 23, 2019 the content of which are incorporated herein in its entirety by reference.

BACKGROUND OF THE INVENTION

1. Field of the Invention

The present invention relates to a method of using a *Parabacteroides goldsteinii* for treating lung cancer.

2. The Prior Art

Cancer is one of the leading causes of human death today. Although the formation of cancer is still not fully understood, it is believed that carcinogenesis or tumorigenesis can be attributed to cells accumulation of exogenous or endogenous factor leading to genetic abnormalities, and then cause the signal transduction pathways in these cells is erroneous and cell division to be out of control, thereby causing the cells to gradually form cancer. Cancer cells are able to evade apoptosis and have the ability to migrate and invade, so cancer cells proliferate and pass through the lymphatic or vascular system to be transferred metastasize to other parts of the body.

Lung cancer can be mainly divided into two types, one is non-small cell lung cancer (NSCLC) and the other is small cell lung cancer (SCLC). Non-small cell lung cancer accounts for about 80% of lung cancer in total. The third most common non-small cell lung cancers in the United States are lung adenocarcinoma/bronchial alveolar carcinoma (35-40%), squamous cell carcinoma (25-30%), and large cell lung cancer (10-15%). Lung cancer is the most easily cured if it is diagnosed at the beginning of the disease. Early cancer means that it has not grown into a large volume or transferred to other parts of the body. The larger or metastatic cancer is more difficult to be treated.

The main methods currently used to treat lung cancer include surgery, radiation therapy, chemical drug therapy, target therapy, and combination therapy. However, the above treatment methods often have side effects; for example, chemical drug treatment could cause nausea and vomiting in patients and infections and bleeding problems in severe one; radiation therapy could also cause nausea and vomiting in patients and hair loss problem in severe one. In addition, traditional treatments are often expensive and not affordable for the most patient. In order to solve the above problems, those having ordinary skill in the art urgently need to develop a novel pharmaceutical or food product having the efficacy of treating lung cancer for the benefit of a large group of people in need thereof.

SUMMARY OF THE INVENTION

To solve the foregoing problem, the objective of the present invention is to provide a method of treating a lung cancer, comprising administering to a subject in need thereof a composition comprising an effective amount of a *Parabacteroides goldsteinii*.

In one embodiment of the present invention, the composition further comprises a metabolite of the *Parabacteroides goldsteinii*.

In one embodiment of the present invention, the *Parabacteroides goldsteinii* is a live bacterium.

In one embodiment of the present invention, the effective amount of the *Parabacteroides goldsteinii* is at least $1 \times 10^9$ CFUs per day.

In one embodiment of the present invention, the lung cancer is a non-small cell lung cancer (NSCLC).

In one embodiment of the present invention, the non-small cell lung cancer is a Lewis lung carcinoma (LLC).

In one embodiment of the present invention, the composition increases a survival rate, a mean survival time and a body weight of the subject with the lung cancer, and inhibits a growth of a lung tumor.

In one embodiment of the present invention, the inhibiting step comprises inhibiting the growth of the lung tumor at different time points.

In one embodiment of the present invention, the composition further comprises other bacteria.

In one embodiment of the present invention, the *Parabacteroides goldsteinii* is *Parabacteroides goldsteinii* DSM32939.

In one embodiment of the present invention, the composition is a pharmaceutical composition or a food product.

In one embodiment of the present invention, the composition further comprises a pharmaceutically acceptable excipient, carrier, adjuvant, or food additive.

In one embodiment of the present invention, the composition is in the form of a spray, a solution, a semi-solid state, a solid state, a gelatin capsule, a soft capsule, a tablet, an oral strip, a chewing gum or a freeze-dried powder preparation.

In summary, the effect of the *Parabacteroides goldsteinii* of the present invention is that the effect of treating lung cancer which is achieved by increasing the survival rate, the mean survival time, and the body weight of the subjects with lung cancer, and inhibiting the growth of the lung tumor.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

Definition

The data provides in the present invention represent approximated, experimental values that vary within a range of ±20%, preferably ±10%, and most preferably ±5%.

Statistical analysis is performed using GraphPad prism 5.01 software (GraphPad Software Inc., San Diego, Calif.). Data are expressed as mean±standard deviation (SD), and differences between groups are statistically analyzed by one-way ANOVA and statistical analysis is performed by Dunnett's multiple comparison test.

According to the present invention, the *Parabacteroides goldsteinii* is a Gram-negative, particularly anaerobic non-spore forming and non-moving bacterium, and is also a probiotic bacterium.

According to the present invention, the probiotic or probiotic bacteria is a microorganism, the cells thereof, the mixed strains, the extracts or the metabolites with a positive effect on the host itself, usually derived from the human body and beneficial to intestinal health. Probiotic or probiotic bacteria can also refer to certain microorganisms that are externally supplemented and are beneficial to the body. Wherein, the metabolite of the probiotic or probiotic bacteria is a substance which is secreted into the bacterial culture solution after being metabolized by the bacteria.

According to the present invention, the operating procedures and parameter conditions for bacterial culture are within the professional literacy and routine techniques of those having ordinary skill in the art.

The "effective amount" describes herein is the amount of the *Parabacteroides goldsteinii* requires for direct treatment of individuals with lung cancer. The effective amount varies depending on the species or individual being treated, but the effective amount can be determined experimentally by, for example, a dose escalation test.

The "metabolite" describes herein is a substance which is secreted into the bacterial culture solution after being metabolized by the bacteria.

The "the bacterial component thereof" describes herein is a derivative substance directly or indirectly related to the bacterium when it is cultured, including but not limited to the metabolic product of the bacterium, the structure of the bacterium, the bacteria-related activity and the inactive ingredient, etc.

The "*Parabacteroides goldsteinii*" describes herein is intended to encompass those of the *Parabacteroides goldsteinii*, which is readily available to those having ordinary skill in the art, for example, the *Parabacteroides goldsteinii* purchased from domestic or foreign depository institutions, and a strain of *Parabacteroides goldsteinii* isolated and purified from a natural source using a microorganism separation method conventionally used in the art.

The "treating" or "treatment" describes herein means alleviating, reducing, ameliorating, relieving, or controlling a disease or one or more clinical signs of a disorder, and lowering, stopping, or reversing the progress of the severity of a condition or a symptom being treated.

According to the present invention, the pharmaceutical composition can be manufactured into a dosage form suitable for parenterally or orally administration using techniques well known to those having skill in the art, including, but not limited to, an injection, for example, sterile aqueous solutions or dispersions, a sterile powder, tablets, a tablet, a lozenge, a pill, a capsule, a dispersible powder or a granule, a solution, a suspension, a emulsion, a syrup, an elixir, a slurry and the like.

According to the present invention, the pharmaceutical composition can be administered by a parenteral route selected from the group consisting of the intraperitoneal injection, the subcutaneous injection, the intramuscular injection, and the intravenous injection.

According to the present invention, the pharmaceutical composition could further comprise a pharmaceutically acceptable carrier that is widely used in pharmaceutical manufacturing techniques. For example, the pharmaceutically acceptable carrier can comprise one or more agents selected from the group consisting of a solvent, an emulsifier, a suspending agent, a decomposer, a binding agent, an excipient, a stabilizing agent, a chelating agent, a diluent, a gelling agent, a preservative, a lubricant, an absorption delaying agent, a liposome, and the like. The selection and quantity of these reagents falls within the professional literacy and routine skills of those having ordinary skill in the art.

According to the present invention, the pharmaceutically acceptable carrier comprises a solvent selected from the group consisting of water, normal saline, phosphate buffered saline (PBS), sugary solution, aqueous solution containing alcohol, and combinations thereof.

According to the present invention, the pharmaceutical composition can be used as a food additive, added by the conventional method in the preparation of the raw material, or added during the production of the food, and matched with any edible material to be made into food products for human and non-human animals.

According to the present invention, the types of the food products include, but are not limited to, beverages, fermented foods, bakery products, health foods, and dietary supplements.

The use of the *Parabacteroides goldsteinii* of the present invention in the treatment of lung cancer can be, but is not limited to, oral administration to the subject in need thereof. The composition can be orally administered along with food; therefore, the preparation of the composition comprising the *Parabacteroides goldsteinii* of the present invention can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *Parabacteroides goldsteinii* of the present invention can further include a pharmaceutically acceptable excipient, carrier, adjuvant, or food additive. The composition is in the form of, but is not limited to a spray gas, a solution, a semi-solid state, a solid, a gelatin capsule, a soft capsule, a tablet, a lozenge, a chewing gum, and/or a freeze-dried powder preparation. Simultaneously, the *Parabacteroides goldsteinii* of the present invention or the composition containing other ingredients can further use in the preparation of a food, a health food, a dietary supplement, or a vaccine composition.

Example 1

Effect of *Parabacteroides goldsteinii* MTS01 on Increasing the Survival Rate of Lung Cancer Mice In the embodiment of the present invention, six-to-eight-week-old, specific pathogen-free, C57BL/6J male mice were purchased from National Applied Research Laboratories, NARLab, Taiwan. All mice were fed ad libitum with chow and water. Animals were housed in a temperature-controlled room (19-23° C.) under a 12 hours dark-light cycle. Animals were housed in a specific pathogen-free facility and were treated in accordance with guidelines from the National Institutes of Health (USA). In the following experiments, C57BL/6J male mice were injected with Lewis Lung Carcinoma (LLC) cells ($1 \times 10^6$ cells) in the tail vein, and then the growth and volume of the tumor were monitored throughout the experiment.

The *Parabacteroides goldsteinii* (hereinafter referred to as *P. goldsteinii*) MTS01 used in the example of the present invention is a kind of probiotic bacteria, which can or treat lung cancer, and is deposited in Deutsche Sammlung von Mikroorganismen und Zellkulturen (DSMZ; Inhoffenstr. 7B, D-38124 Braunschweig, Germany) on Oct. 29, 2018, and the number is DSM 32939. The *Parabacteroides goldsteinii* is an obligate anaerobe that needs to be cultured in an anaerobic incubator at 37° C. for about 48 hours, wherein the culturing system contains 10% $CO_2$, 10% $H_2$, and 80% $N_2$. The liquid culture medium of the *Parabacteroides goldsteinii* is NIH thioglycollate broth (TGC II) (purchased from BD, USA, No. 225710), and the solid culture medium is Anaerobic blood agar plate (Ana. BAP) (purchased from CREATIVE LIFESCIENCES, Taiwan). The *Parabacteroides goldsteinii* is stored in a −80° C. refrigerator for a long-term preservation, and the protective liquid is 25% glycerin. It does not need special cooling treatment and can be stored by freeze drying to stabilize its activity.

The *Parabacteroides distasonis* (hereinafter referred to as *P. distasonis*) used in the example of the present invention was purchased from American Type Culture Collection, and the number is ATCC 8503. YCFA medium was used for culturing, wherein the *Parabacteroides distasonis* was cultured in 50 mL YCFA at 37° C. in an anaerobic incubator for 24 hr. The cell suspension for oral administration was prepared by suspending the cultured bacterial cells in oxygen-free PBS with a final cell density of $1 \times 10^9$ CFU. 100 μL of the suspension solution was given daily.

The non-small cell lung cancer, NSCLC, used in the example of the present invention is Lewis lung cancer (LLC) cells (purchased from ATCC, and the number is ATCC®CRL 1642™). The LLC cells were maintained in Dulbecco's modified Eagle's medium, DMEM, (purchased from Gibco, USA) supplemented with 10% fetal bovine serum (purchased from Gibco, USA), 100 U/mL of penicillin, and 100 μg/mL of streptomycin, and were incubated at 37° C. in a humidified atmosphere containing 5% $CO_2$.

Male C57BL/6J mice were randomly divided into the 4 groups (n=10 for each group), including the normal control group (CTL), the pathological control group (LLC), the experimental group (LLC+*P. goldsteinii* MTS01), and the comparison group (LLC+*P. distasonis*). The mice in the normal control group were treated with sterile drinking water and fed with PBS oral gavage once per day for 3 weeks; the mice in the pathological control group were treated with Neomycin (1 g/L) in drinking water for 7 days, followed by LLC cells ($1 \times 10^6$) intravenous injection via tail vein and fed with PBS by oral gavage once per day during the entire period of experiment; the mice in the experimental group were treated with Neomycin (1 g/L) in drinking water for 7 days, followed by LLC cells ($1 \times 10^6$) intravenous injection via tail vein and treated with *Parabacteroides goldsteinii* MTS01 ($1 \times 10^9$ CFU) once per day by oral gavage during the entire period of experiment; the mice in the comparison group were treated with Neomycin (1 g/L) in drinking water for 7 days, followed by LLC cells ($1 \times 10^6$) intravenous injection via tail vein and treated with *Parabacteroides distasonis* ($1 \times 10^9$ CFU) once per day by oral gavage during the entire period of experiment. The results of this example were represented by three independent experiments (n=10) and the results were shown in FIG. 1.

Figure 1:
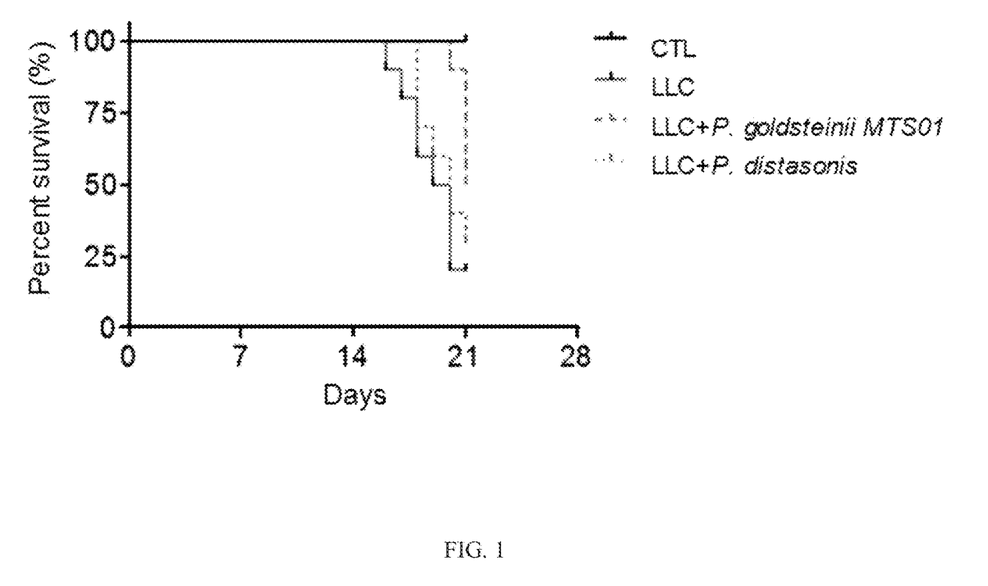
FIG. 1 shows that the effect of the *Parabacteroides goldsteinii* MTS01 on increasing the survival rate of lung cancer mice.

The results of the effect of the *Parabacteroides goldsteinii* MTS01 on increasing the survival rate of lung cancer mice were shown in FIG. 1. As showing in FIG. 1, after 21 days of intravenous injection of LLC cells, the survival rate of the mice in the pathological control group was 20%, and the survival rate of the mice in the experimental group was 50%, which was higher than that of the mice in the comparison group. The mice in the normal control were healthy and alive throughout the experiment. The results indicate that the *Parabacteroides goldsteinii* strain MTS01 of the present invention can increase the survival rate of mice with lung cancer.

Example 2

Effect of *Parabacteroides goldsteinii* MTS01 on Increasing the Mean Survival Time of Lung Cancer Mice The experimental animals, the *Parabacteroides goldsteinii*, the *Parabacteroides distasonis*, and the type and the culturing method of the Lewis lung cancer were the same as those described in example 1.

Male C57BL/6J mice were randomly divided into the 4 groups (n=10 for each group), including the normal control group (CTL), the pathological control group (LLC), the experimental group (LLC+*P. goldsteinii* MTS01), and the comparison group (LLC+*P. distasonis*). The mice in the normal control group were treated with sterile drinking water and fed with PBS oral gavage once per day for 4 weeks; the mice in the pathological control group were treated with Neomycin (1 g/L) in drinking water for 7 days, followed by LLC cells ($1 \times 10^6$) intravenous injection via tail vein and fed with PBS by oral gavage once per day during the entire period of experiment; the mice in the experimental group were treated with Neomycin (1 g/L) in drinking water for 7 days, followed by LLC cells ($1 \times 10^6$) intravenous injection via tail vein and treated with *Parabacteroides goldsteinii* MTS01 ($1 \times 10^9$ CFU) once per day by oral gavage during the entire period of experiment; the mice in the comparison group were treated with Neomycin (1 g/L) in drinking water for 7 days, followed by LLC cells ($1 \times 10^6$) intravenous injection via tail vein and treated with *Parabacteroides distasonis* ($1 \times 10^9$ CFU) once per day by oral gavage during the entire period of experiment. The results of this example were represented by three independent experiments (n=10) and the results were shown in FIG. 2.

Figure 2:
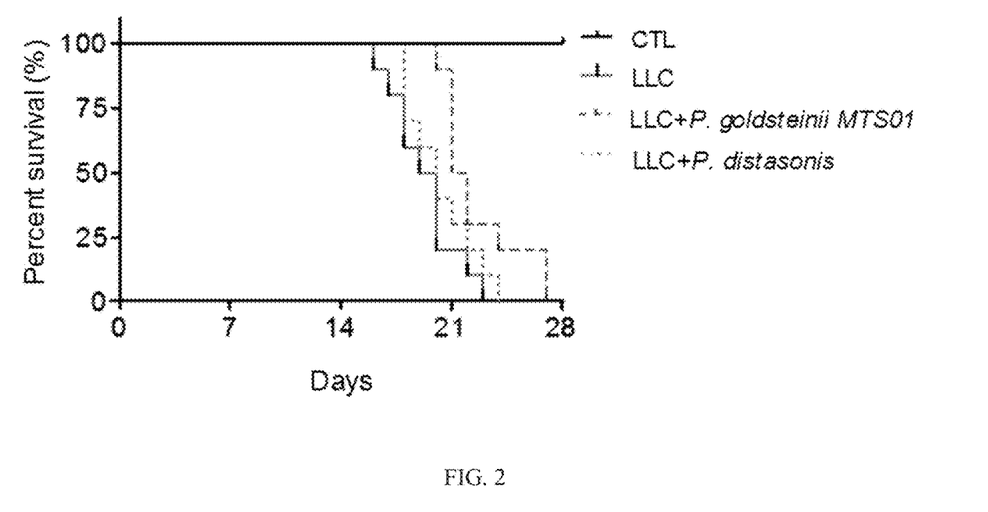
FIG. 2 shows that the effect of the *Parabacteroides goldsteinii* MTS01 on increasing the mean survival time of lung cancer mice.

The results of the effect of the *Parabacteroides goldsteinii* MTS01 on increasing the mean survival time of lung cancer mice were shown in FIG. 2. As showing in FIG. 2, the mean survival time of the mice in the experimental group was 22.6 days, which was higher than that of the mice in the pathological control group (19.3 days) (P<0.01) and that of the mice in the comparison group. The mice in the normal control were healthy and alive throughout the experiment. The results indicate that the *Parabacteroides goldsteinii* strain MTS01 of the present invention can increase the mean survival time of mice with lung cancer.

Example 3

Effect of *Parabacteroides goldsteinii* MTS01 on Increasing the Body Weight of Lung Cancer Mice The experimental animals, the *Parabacteroides goldsteinii*, the *Parabacteroides distasonis*, and the type and the culturing method of the Lewis lung cancer were the same as those described in example 1.

Male C57BL/6J mice were randomly divided into the 4 groups (n=10 for each group), including the normal control group (CTL), the pathological control group (LLC), the experimental group (LLC+*P. goldsteinii* MTS01), and the comparison group (LLC+*P. distasonis*). The mice in the normal control group were treated with sterile drinking water and fed with PBS oral gavage once per day for 4 weeks; the mice in the pathological control group were treated with Neomycin (1 g/L) in drinking water for 7 days, followed by LLC cells ($1\times10^6$) intravenous injection via tail vein and fed with PBS by oral gavage once per day during the entire period of experiment; the mice in the experimental group were treated with Neomycin (1 g/L) in drinking water for 7 days, followed by LLC cells ($1\times10^6$) intravenous injection via tail vein and treated with *Parabacteroides goldsteinii* MTS01 ($1\times10^9$ CFU) once per day by oral gavage during the entire period of experiment; the mice in the comparison group were treated with Neomycin (1 g/L) in drinking water for 7 days, followed by LLC cells ($1\times10^6$) intravenous injection via tail vein and treated with *Parabacteroides distasonis* ($1\times10^9$ CFU) once per day by oral gavage during the entire period of experiment.

In order to study the effect of the *Parabacteroides distasonis* MTS01 on improving the body weight loss in subjects caused by LLC, the body weight of each group of mice was monitored weekly for 4 weeks during the experiment. The final body weight at week 4 subtracted the starting weight at week 0 as the value of the body weight gain of each group of mice. The value of body weight gain was divided by the starting body weight and expressed as a percentage to calculate the body weight change rate of each group of mice. The results of the example were shown in FIG. 3.

Figure 3:
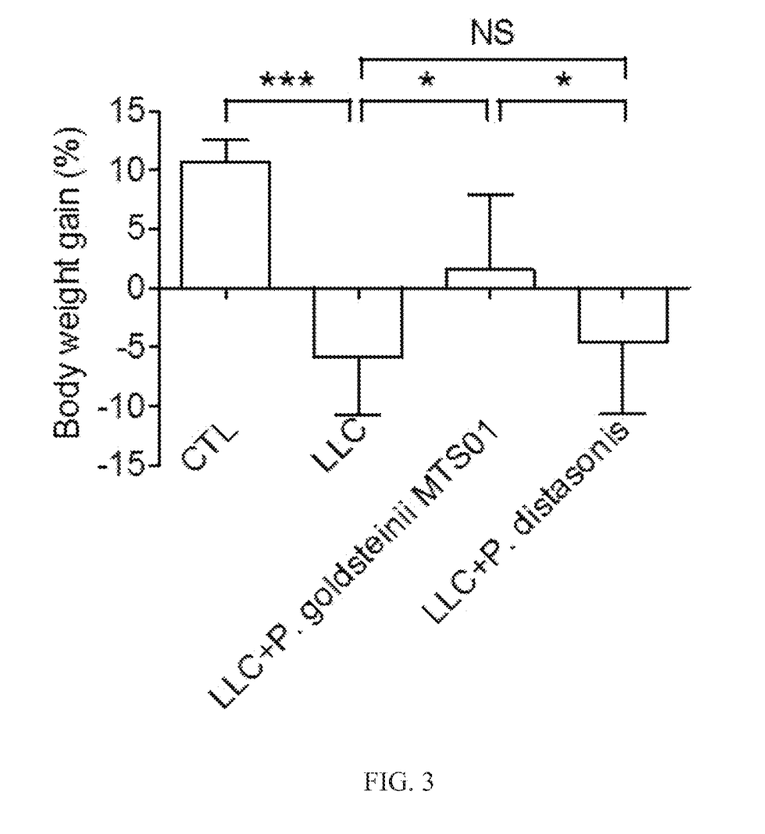
FIG. 3 shows that the effect of the *Parabacteroides goldsteinii* MTS01 on increasing the body weight of lung cancer mice. *$p<0.05$; ***$p<0.001$; NS means no significant difference.

The results of the effect of the *Parabacteroides goldsteinii* MTS01 on increasing the body weight of lung cancer mice were shown in FIG. 3. As showing in FIG. 3, the body weight gain of the mice in the pathological control group was significantly lower than that of the mice in the normal control group. However, compared with the pathological control group, the body weight gain of the mice in the experimental group mice was significantly increased with the simultaneously fed with the *Parabacteroides goldsteinii* MTS01 of the present invention, whereas the mice in the comparison group did not show this phenomenon. The results indicate that the *Parabacteroides goldsteinii* strain MTS01 of the present invention can effectively improve the body weight loss in the subjects caused by LLC.

Example 4

Effect of *Parabacteroides goldsteinii* MTS01 on Inhibiting the Growth of the Lung Tumor The experimental animals, the *Parabacteroides goldsteinii*, the *Parabacteroides distasonis*, and the type and the culturing method of the Lewis lung cancer were the same as those described in example 1.

Male C57BL/6J mice were randomly divided into the 4 groups (n=10 for each group), including the normal control group (CTL), the pathological control group (LLC), the experimental group (LLC+*P. goldsteinii* MTS01), and the comparison group (LLC+*P. distasonis*). The mice in the normal control group were treated with sterile drinking water and fed with PBS oral gavage once per day for 3 weeks; the mice in the pathological control group were treated with Neomycin (1 g/L) in drinking water for 7 days, followed by LLC cells ($1\times10^6$) intravenous injection via tail vein and fed with PBS by oral gavage once per day during the entire period of experiment; the mice in the experimental group were treated with Neomycin (1 g/L) in drinking water for 7 days, followed by LLC cells ($1\times10^6$) intravenous injection via tail vein and treated with *Parabacteroides goldsteinii* MTS01 ($1\times10^9$ CFU) once per day by oral gavage during the entire period of experiment; the mice in the comparison group were treated with Neomycin (1 g/L) in drinking water for 7 days, followed by LLC cells ($1\times10^6$) intravenous injection via tail vein and treated with *Parabacteroides distasonis* ($1\times10^9$ CFU) once per day by oral gavage during the entire period of experiment. The results of this example were represented by three independent experiments (n=10).

After fed with the *Parabacteroides distasonis* MTS01 by oral gavage for 21 days, each group of mice was sacrificed, and the lungs were removed and the appearance of the lungs was observed. The results of the experiment were shown in FIG. 4.

Figure 4:
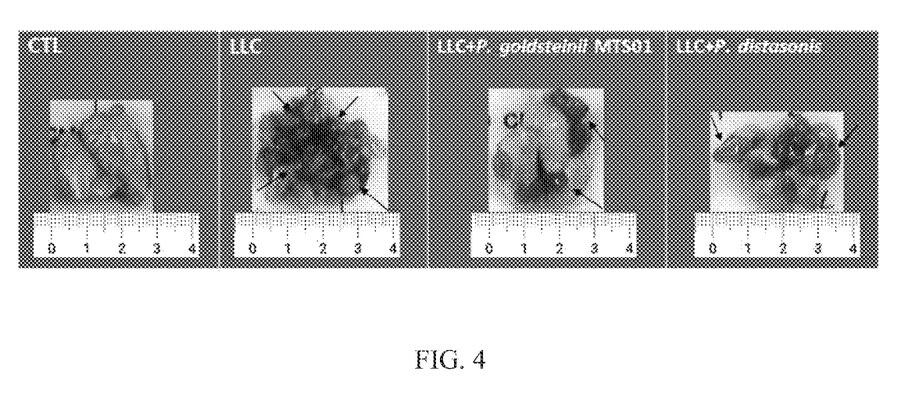
FIG. 4 shows that the appearance of the effect of the *Parabacteroides goldsteinii* MTS01 on inhibiting the growth of the lung tumor.

The appearance results of the effect of the *Parabacteroides goldsteinii* MTS01 on inhibiting the growth of the lung tumor were shown in FIG. 4. As showing in FIG. 4, the solid tumors (as indicated by the arrows) were spotted on multiple sites in the group bearing with LLC. Compared with the pathological control group, the number of lung tumors in the mice of the experimental group was significantly reduced, while the comparison group did not show the phenomena. The results indicate that the *Parabacteroides goldsteinii* strain MTS01 of the present invention can inhibit the growth of lung tumor.

Next, the lung leaves of the mice in the normal control group (CTL), the pathological control group (LLC), and the experimental group (LLC+*P. goldsteinii* MTS01) were fixed in 10% neutral-buffered formalin, and then embedded in paraffin and thin sections with a thickness of 4 mm were prepared and stained with hematoxylin and eosin (H&E). Thereafter, the stained lungs were histologically examined using a slide scanner and the entire lung lobe was photographed (Olympus VS120). Representative images of whole slide scan and 500 μm or 250 μm optical zoom using H&E-stained lung sections. The results of the experiment were shown in FIG. 5.

Figure 5:
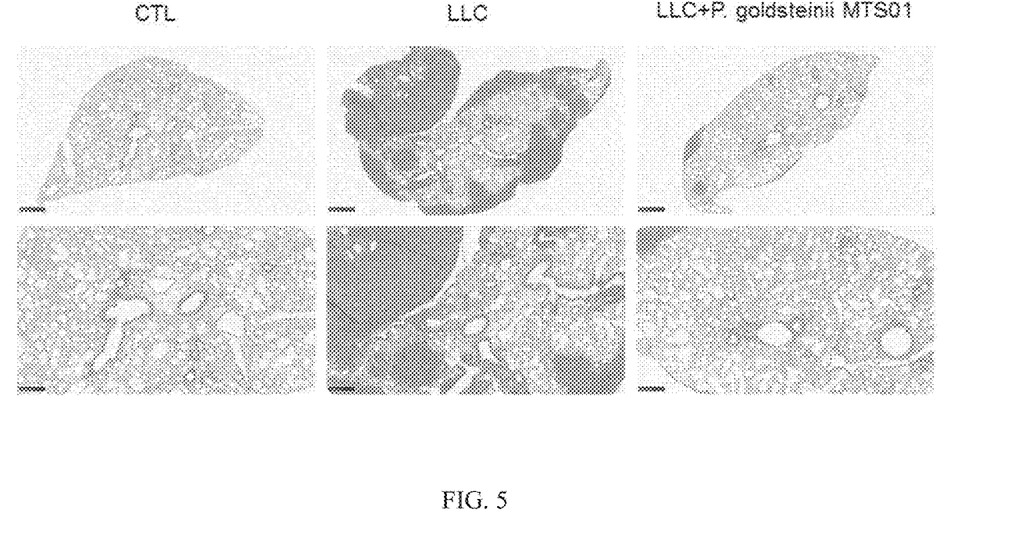
FIG. 5 shows that the H&F stained images of the effect of the *Parabacteroides goldsteinii* MTS01 on inhibiting the growth of the lung tumor.

The H&E stained results of the effect of the *Parabacteroides goldsteinii* MTS01 on inhibiting the growth of the lung tumor were shown in FIG. 5. As showing in FIG. 5, compared with the normal control group, the number of lung tumors in the mice of the pathological control group was significantly increased. However, compared with the pathological control group, the number of lung tumors in the mice of the experimental group was significantly reduced. The results indicate that the *Parabacteroides goldsteinii* strain MTS01 of the present invention can inhibit the growth of lung tumor.

Figure 6:
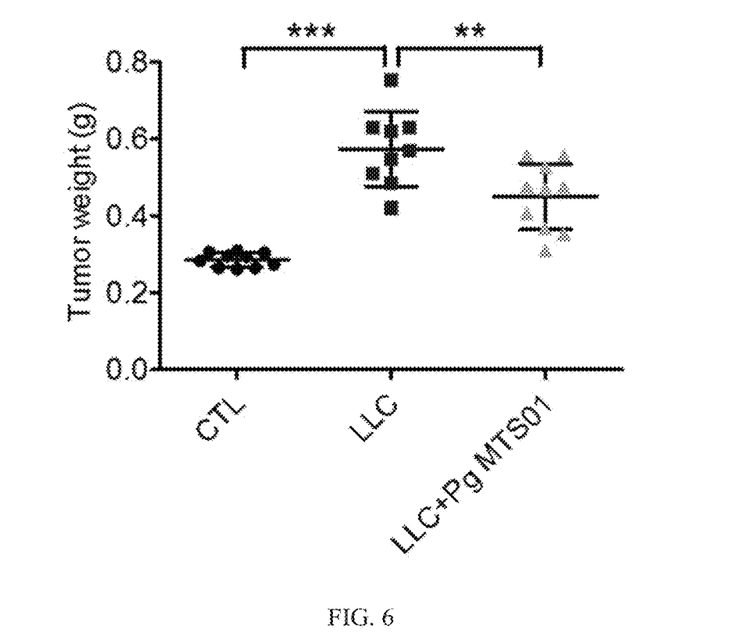
FIG. 6 shows that the effect of the *Parabacteroides goldsteinii* MTS01 on inhibiting the growth of the lung tumor. p<0.01; *p<0.001.

Next, the lung tumors of the mice in the normal control group (CTL), the pathological control group (LLC), and the experimental group (LLC+Pg MTS01) were weighed, and the results of the experiment were shown in FIG. 6.

The data results of the effect of the *Parabacteroides goldsteinii* MTS01 on inhibiting the growth of the lung tumor were shown in FIG. 6. As showing in FIG. 6, compared with the normal control group, the lung tumor weight of the mice in the pathological control group was significantly increased. However, compared with the pathological control group, the lung tumor weight of the mice in the experimental group was significantly reduced. The results indicate that the *Parabacteroides goldsteinii* MTS01 of the present invention can inhibit the growth of the tumor growth in the mouse model with lung tumors.

Example 5

In Vivo Effect of *Parabacteroides goldsteinii* MTS01 on Inhibiting Lung Cancer at Different Time Points The experimental animals, the *Parabacteroides goldsteinii*, the *Parabacteroides distasonis*, and the type and the culturing method of the Lewis lung cancer were the same as those described in example 1.

Male C57BL/6J mice were randomly divided into the 3 groups (n=10 for each group), including the normal control group (CTL), the pathological control group (LLC), and the experimental group (LLC+Pg MTS01). Wherein, the mice in the normal control group were treated with sterile drinking water and fed with PBS oral gavage once per day; the mice in the pathological control group were treated with Neomycin (1 g/L) in drinking water for 7 days, followed by LLC cells ($1\times10^6$) intravenous injection via tail vein and fed with PBS by oral gavage once per day during the entire period of experiment; the mice in the experimental group were treated with Neomycin (1 g/L) in drinking water for 7 days, followed by LLC cells ($1\times10^6$) intravenous injection via tail vein and treated with *Parabacteroides goldsteinii* MTS01 ($1\times10^9$ CFU) once per day by oral gavage during the entire period of experiment. The results of this example were represented by three independent experiments (n=10).

At the day 0, 7, 14, and 21 after implantation of LLC cells, the mice of each group were anesthetized with isoflurane and intraperitoneally injected with firefly D-luciferin (15 mg/mL in PBS; Gold Biotechnology), and then were imaged with a cooled charge-coupled device (CCD) camera (IVIS; PerkinElmer) after 7 minutes. In vivo imaging was performed with IVIS Lumina XR Imaging system (PerkinElmer). The luciferin dose was 150 mg/kg. The results of the example were shown in FIG. 7 to FIG. 10. The scale indicates luminescent intensity in terms of radiant efficiency.

Figure 7:
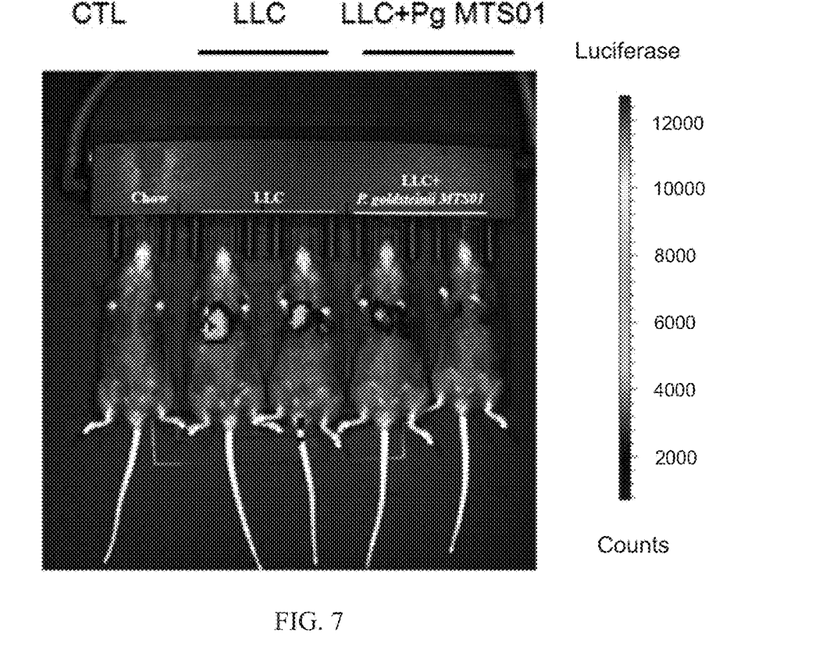
FIG. 7 shows that the bioluminescence images in vivo effect of *Parabacteroides goldsteinii* MTS01 on inhibiting lung cancer after Lewis Lung Carcinoma cells (LLC) implanted on the 7th day.

The bioluminescence imaging results of in vivo effect of *Parabacteroides goldsteinii* MTS01 on inhibiting lung cancer after LLC cells implanted on the 7th day were shown in FIG. 7. As showing in FIG. 7, compared with the normal control group, the luminescent intensity measured from the mice in the pathological control group was significantly increased. However, compared with the pathological control group, the luminescent intensity measured from the mice in the experimental group was significantly reduced. The results indicate that the *Parabacteroides goldsteinii* MTS01 of the present invention has an effect of inhibiting lung cancer after LLC cells implanted on the 7th day in vivo.

Figure 8:
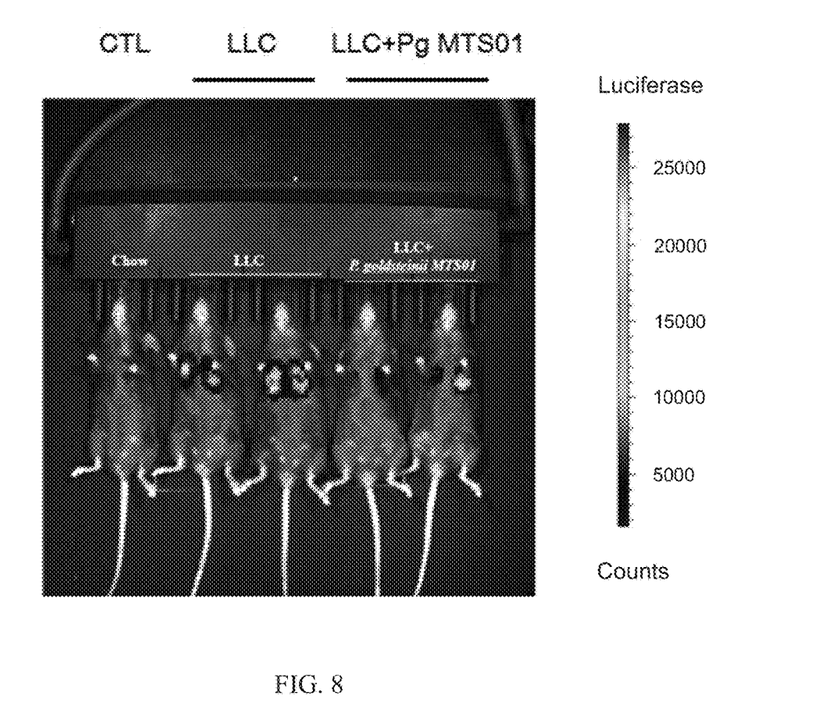
FIG. 8 shows that the bioluminescence images in vivo effect of *Parabacteroides goldsteinii* MTS01 on inhibiting lung cancer after Lewis Lung Carcinoma cells (LLC) implanted on the 14th day.

The bioluminescence imaging results of in vivo effect of *Parabacteroides goldsteinii* MTS01 on inhibiting lung cancer after LLC cells implanted on the 14th day were shown in FIG. 8. As showing in FIG. 8, compared with the normal control group, the luminescent intensity measured from the mice in the pathological control group was significantly increased. However, compared with the pathological control group, the luminescent intensity measured from the mice in the experimental group was significantly reduced. The results indicate that the *Parabacteroides goldsteinii* MTS01 of the present invention has an effect of inhibiting lung cancer after LLC cells implanted on the 14th day in vivo.

Figure 9:
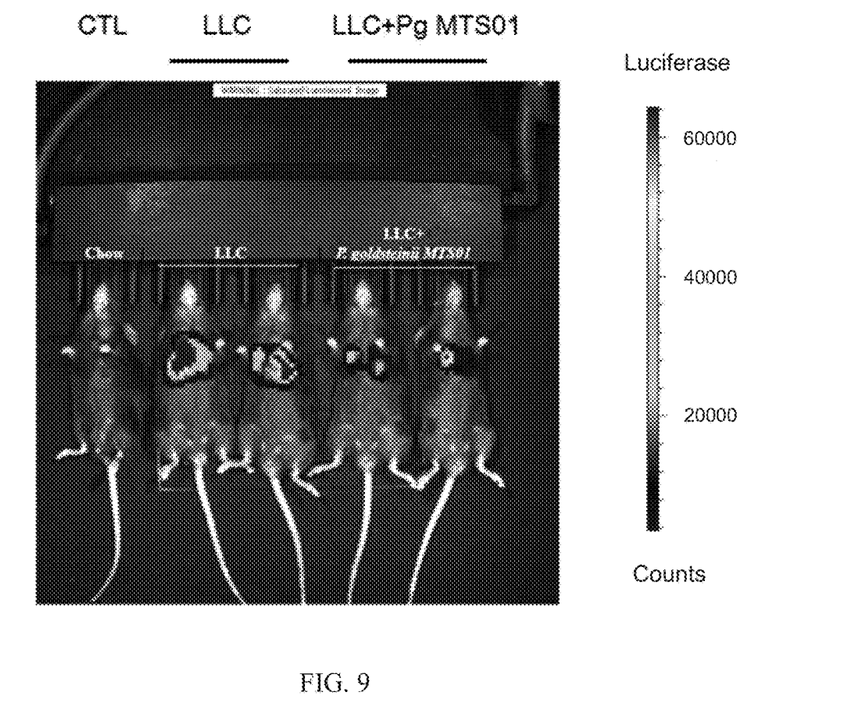
FIG. 9 shows that the bioluminescence images in vivo effect of *Parabacteroides goldsteinii* MTS01 on inhibiting lung cancer after Lewis Lung Carcinoma cells (LLC) implanted on the 21st day.

The bioluminescence imaging results of in vivo effect of *Parabacteroides goldsteinii* MTS01 on inhibiting lung cancer after LLC cells implanted on the 21st day were shown in FIG. 9. As showing in FIG. 9, compared with the normal control group, the luminescent intensity measured from the mice in the pathological control group was significantly increased. However, compared with the pathological control group, the luminescent intensity measured from the mice in the experimental group was significantly reduced. The results indicate that the *Parabacteroides goldsteinii* MTS01 of the present invention has an effect of inhibiting lung cancer after LLC cells implanted on the 21st day in vivo.

Figure 10:
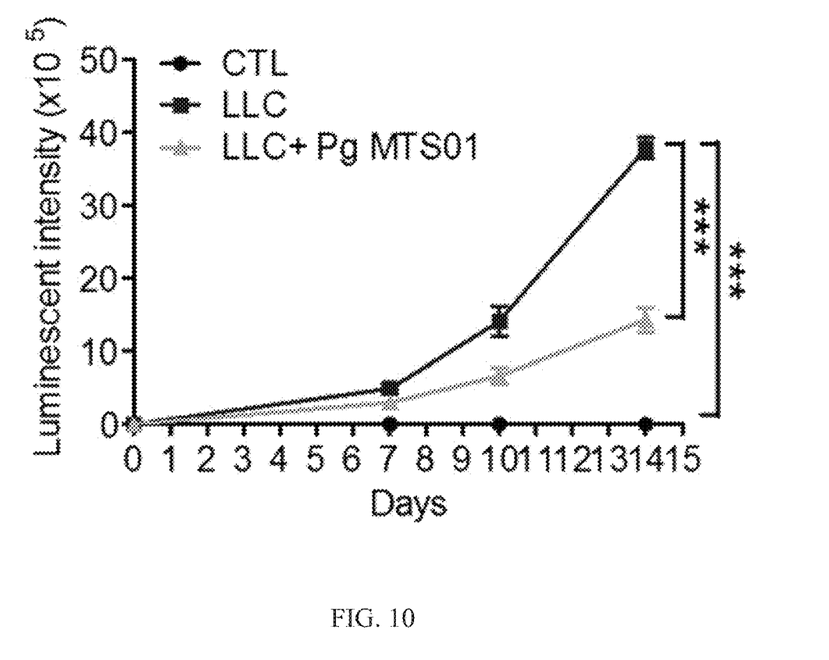
FIG. 10 shows that the in vivo effect of the *Parabacteroides goldsteinii* MTS01 on inhibiting lung cancer at different time points. ***p<0.001.

The results of in vivo effect of the *Parabacteroides goldsteinii* MTS01 on inhibiting lung cancer at different time points were shown in FIG. 10. As showing in FIG. 10, compared with the normal control group, the luminescent intensity measured from the mice in the pathological control group increased significantly as the time of LLC cells implantation. However, compared with the pathological control group, though the luminescent intensity measured from the mice in the experimental group increased as the time of LLC cells implantation, but the increase range was significantly reduced. The results indicate that the *Parabacteroides goldsteinii* MTS01 of the present invention has an effect of inhibiting lung cancer at different time points in vivo.

In summary, the effect of the *Parabacteroides goldsteinii* of the present invention is that the effect of treating lung cancer which is achieved by increasing the survival rate, the mean survival time, and the body weight of the subjects with lung cancer, and inhibiting the growth of the lung tumor.

The above description is by way of example only and not as a limitation. Any equivalent modifications or alterations to the spirit and scope of the invention are intended to be included in the scope of the appended claims.

What is claimed is:

1. A method of treating a lung cancer, comprising administering to a subject in need thereof a composition comprising an effective amount of a *Parabacteroides goldsteinii*; wherein the *Parabacteroides goldsteinii* is *Parabacteroides goldsteinii* DSM32939.

2. The method according to claim 1, wherein the composition further comprises a metabolite of the *Parabacteroides goldsteinii*.

3. The method according to claim 1, wherein the *Parabacteroides goldsteinii* is a live bacterium.

4. The method according to claim 1, wherein the effective amount of the *Parabacteroides goldsteinii* is at least $1\times10^9$ CFUs per day.

5. The method according to claim 1, wherein the lung cancer is a non-small cell lung cancer.

6. The method according to claim 5, wherein the non-small cell lung cancer is a Lewis lung carcinoma.

7. The method according to claim 1, wherein the composition increases a survival rate, a mean survival time and a body weight of the subject with the lung cancer, and inhibits a growth of a lung tumor.

8. The method according to claim 7, wherein inhibiting comprises inhibiting the growth of the lung tumor at different time points.

9. The method according to claim 1, wherein the composition further comprises other bacteria.

10. The method according to claim 1, wherein the composition is a pharmaceutical composition or a food product.

11. The method according to claim 10, wherein the composition further comprises a pharmaceutically acceptable excipient, carrier, adjuvant, or food additive.

12. The method according to claim 1, wherein the composition is in the form of a spray, a solution, a semi-solid state, a solid state, a gelatin capsule, a soft capsule, a tablet, an oral strip, a chewing gum or a freeze-dried powder preparation.

* * * * *